US009513221B2

(12) United States Patent
Ishihara

(10) Patent No.: US 9,513,221 B2
(45) Date of Patent: Dec. 6, 2016

(54) FLUORESCENCE OBSERVATION APPARATUS

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 619 days.

(21) Appl. No.: 13/950,376

(22) Filed: Jul. 25, 2013

(65) Prior Publication Data

US 2013/0307952 A1 Nov. 21, 2013

Related U.S. Application Data

(63) Continuation of application No. PCT/JP2012/051814, filed on Jan. 27, 2012.

(30) Foreign Application Priority Data

Jan. 31, 2011 (JP) ................................ 2011-019161

(51) Int. Cl.
*G01N 21/64* (2006.01)
*A61B 1/04* (2006.01)
(Continued)

(52) U.S. Cl.
CPC ....... *G01N 21/6456* (2013.01); *A61B 1/00006* (2013.01); *A61B 1/00009* (2013.01);
(Continued)

(58) Field of Classification Search
CPC ............ H04N 5/347; H04N 2005/2255; A61B 1/00009; A61B 1/043
See application file for complete search history.

(56) References Cited

U.S. PATENT DOCUMENTS 6,529,768 B1 * 3/2003 Hakamata .......... A61B 1/00009
600/310
2005/0010081 A1 * 1/2005 Doguchi ............ A61B 1/00009
600/109
(Continued)

FOREIGN PATENT DOCUMENTS

EP 0 920 831 A1 6/1999
EP 2 679 136 A1 1/2014
(Continued)

OTHER PUBLICATIONS

International Search Report dated May 15, 2012 issued in PCT/JP2012/051814.
(Continued)

*Primary Examiner* — Obafemi Sosanya
(74) *Attorney, Agent, or Firm* — Scully, Scott, Murphy & Presser, P.C.

(57) ABSTRACT

Observation is performed at a more appropriate sensitivity without causing deterioration of the image quality. Provided is a fluorescence observation apparatus including an excitation light source that emits excitation light to be radiated onto an imaging subject; a fluorescence-image acquisition portion that is provided with an imaging device that acquires fluorescence images by capturing fluorescence generated at the imaging subject due to the irradiation with the excitation light emitted from the excitation light source; and a sensitivity adjusting portion that adjusts an number of pixels for binning summing and/or an exposure time for the imaging device on the basis of luminance information of the fluorescence image acquired by the imaging device of the fluorescence-image acquisition portion so that an SN ratio of the fluorescence image becomes equal to or higher than a predetermined threshold.

13 Claims, 18 Drawing Sheets

(51) Int. Cl.
  *A61B 5/00* (2006.01)
  *A61B 1/00* (2006.01)
  *H04N 5/347* (2011.01)
  *H04N 5/235* (2006.01)
  *H04N 5/225* (2006.01)

(52) U.S. Cl.
  CPC ............ *A61B 1/043* (2013.01); *A61B 5/0071* (2013.01); *G01N 21/6486* (2013.01); *H04N 5/2353* (2013.01); *H04N 5/347* (2013.01); *H04N 2005/2255* (2013.01)

(56) References Cited

U.S. PATENT DOCUMENTS

2006/0082646 A1   4/2006   Abe et al.
2010/0245619 A1   9/2010   Watanabe et al.

FOREIGN PATENT DOCUMENTS

| EP | 2 679 137 A1 | 1/2014 |
| JP | 11-122540 A | 4/1999 |
| JP | 2001-137175 A | 5/2001 |
| JP | 2006-115964 A | 5/2006 |
| JP | 2010-220892 A | 10/2010 |
| JP | 2010-263949 A | 11/2010 |
| WO | WO 2008/143246 A1 | 11/2008 |
| WO | 2010/110138 A1 | 9/2010 |
| WO | 2013/035738 A1 | 3/2013 |

OTHER PUBLICATIONS

Extended Supplementary European Search Report dated Jan. 24, 2014 from related European Application No. 12 74 1766.5.

\* cited by examiner

| NUMBER OF PIXELS FOR BINNING AND SUMMING | INCIDENT LIGHT LEVEL (photon/$\mu m^2$) |
|---|---|
| 1×1 | 100~ |
| 2×2 | 35~100 |
| 4×4 | 15~35 |
| 6×6 | 8.5~15 |
| 8×8 | 6.5~8.5 |
| 10×10 | ~6.5 |

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~13000 | 4330~6500 | | |
| 2×2 | | | 1458~4300 | | |
| 4×4 | | | 625~1458 | | |
| 6×6 | | | 375~625 | | |
| 8×8 | | | 250~375 | | |
| 10×10 | | | 208~250 | 100~208 | ~100 |

| | INCIDENT LIGHT LEVEL (photon/$\mu m^2$) | | |
|---|---|---|---|
| NUMBER OF PIXELS FOR BINNING AND SUMMING \ THRESHOLD | 6 | 10 | 15 |
| 1×1 | 46~ | 100~ | 206~ |
| 2×2 | 18~46 | 35~100 | 64~206 |
| 4×4 | 8~18 | 15~35 | 24~64 |
| 6×6 | 5~8 | 8.5~15 | 15~24 |
| 8×8 | 3.6~5 | 6.5~8.5 | 10~15 |
| 10×10 | ~3.6 | ~6.5 | ~10 |

FIG. 13

| CONTRAST T/C | SN RATIO THRESHOLD $S^3$ |
|---|---|
| ~1.5 | 15 |
| 1.5~3 | 10 |
| 3~ | 6 |

FIG. 15

| LUMINANCE REPRESENTATIVE VALUE OF GRADATION VALUE D / EXPOSURE TIME t | SN RATIO THRESHOLD S/N |
|---|---|
| ~100000 | 15 |
| 100000~300000 | 10 |
| 300000~ | 6 |

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~13000 | 4330~6500 | | |
| 2×2 | | | 1458~4330 | | |
| 4×4 | | | 625~1458 | | |
| 6×6 | | | 375~625 | 180~375 | 100~180 |
| 8×8 | | | | | 70~100 |
| 10×10 | | | | | ~70 |

| NUMBER OF PIXELS FOR BINNING AND SUMMING | IMAGING-SURFACE ILLUMINANCE (photon/sec/$\mu m^2$) | | | | |
|---|---|---|---|---|---|
| | EXPOSURE TIME (msec) | | | | |
| | 8 | 16 | 24 | 50 | 100 |
| 1×1 | 13000~ | 6500~13000 | | | |
| 2×2 | | 2200~6500 | | | |
| 4×4 | | 875~2200 | | | |
| 6×6 | | 560~875 | | | |
| 8×8 | | 380~560 | | | |
| 10×10 | | 310~380 | 208~310 | 100~208 | ~100 |

| NUMBER OF PIXELS FOR BINNING AND SUMMING | IMAGING-SURFACE ILLUMINANCE (photon/sec/μm²) | | | | |
|---|---|---|---|---|---|
| | EXPOSURE TIME (msec) | | | | |
| | 8 | 16 | 24 | 50 | 100 |
| 1×1 | 13000~ | 6500~13000 | 4330~6500 | 2080~4330 | 1040~2080 |
| 2×2 | | | | | 270~1040 |
| 4×4 | | | | | 150~270 |
| 6×6 | | | | | 100~150 |
| 8×8 | | | | | 70~100 |
| 10×10 | | | | | ~70 |

| NUMBER OF PIXELS FOR BINNING AND SUMMING | IMAGING-SURFACE ILLUMINANCE (photon/sec/μm²) | | | | |
|---|---|---|---|---|---|
| | EXPOSURE TIME (msec) | | | | |
| | 8 | 16 | 24 | 50 | 100 |
| 1×1 | 13000~ | 6500~13000 | | | |
| 2×2 | | 2200~6500 | | | |
| 4×4 | | 875~2200 | | | |
| 6×6 | | 560~875 | 375~560 | | |
| 8×8 | | | 250~375 | | |
| 10×10 | | | 208~250 | 100~208 | ~100 |

FLUORESCENCE OBSERVATION APPARATUS

CROSS-REFERENCE TO RELATED APPLICATIONS

This is a continuation of International Application PCT/JP2012/051814, with an international filing date of Jan. 27, 2012, which is hereby incorporated by reference herein in its entirety.

BACKGROUND OF THE INVENTION

1. Field of the Invention

The present invention relates to a fluorescence observation apparatus.

2. Description of Related Art

In the related art, there is a known technique for fluorescence observation apparatuses, such as fluorescence endoscopes, in which the number of pixels for binning summing and the exposure time are changed in accordance with the brightness of an image in order to detect weak fluorescence coming from an imaging subject, and thus, observation is performed by increasing the sensitivity by increasing the number of pixels for binning summing and increasing the exposure time when the fluorescence level is low (for example, see PCT International Publication No. WO 2008/143246).

A fluorescence observation apparatus according to an aspect of the present invention provides a fluorescence observation apparatus including an excitation light source that emits excitation light to be radiated onto an imaging subject; a fluorescence-image acquisition portion that is provided with an imaging device that acquires a fluorescence image by capturing fluorescence generated at the imaging subject due to the irradiation with the excitation light emitted from the excitation light source; and a sensitivity adjusting portion that adjusts a number of pixels for binning summing and/or an exposure time for the imaging device on the basis of luminance information of the fluorescence image acquired by the imaging device of the fluorescence-image acquisition portion so that an SN ratio of the fluorescence image becomes equal to or higher than a predetermined threshold.

With the above-described aspect, fluorescent substances in the imaging subject are excited due to the irradiation of the imaging subject with the excitation light emitted from the excitation light source, and the fluorescence image is acquired by the imaging device of the fluorescence-image acquisition portion by capturing the generated fluorescence. Although the acquired fluorescence image contains noise caused in the imaging device and noise caused in an image-generating circuit, the amounts thereof have a certain correspondence to the incident light level on the imaging device, and the incident light level can be estimated based on the luminance information of the fluorescence image acquired by the imaging device.

In the above-described aspect, the sensitivity adjusting portion may adjust the number of pixels for binning summing for the imaging device on the basis of the luminance information of the fluorescence image acquired by the imaging device so that the number of pixels for binning summing takes a lowest value at which the SN ratio becomes equal to or higher than the predetermined threshold.

In the above-described aspect, the sensitivity adjusting portion may be provided with an incident-light-level calculating portion that calculates an incident light level on the imaging device based on the luminance information; and a storage portion that stores a correspondence relationship between the incident light level on the imaging device and the number of pixels for binning summing, wherein the number of pixels for binning summing may be determined based on the correspondence relationship stored in the storage portion by using the incident light level calculated by the incident-light-level calculating portion.

The above-described aspect may be provided with a threshold setting portion that sets the threshold, wherein the storage portion may store a correspondence relationship between the incident light level on the imaging device and the SN ratio for each number of pixels for binning summing.

In the above-described aspect, the sensitivity adjusting portion may adjust the exposure time for the imaging device on the basis of the luminance information of the fluorescence image acquired by the imaging device so that the exposure time takes the lowest value at which the SN ratio becomes equal to or higher than the predetermined threshold.

In the above-described aspect, the sensitivity adjusting portion may be provided with an incident-light-level calculating portion that calculates an incident light level on the imaging device based on the luminance information; and a storage portion that stores a correspondence relationship between the incident light level on the imaging device and the exposure time, wherein the exposure time may be determined based on the correspondence relationship stored in the storage portion by using the incident light level calculated by the incident-light-level calculating portion.

The above-described aspect may be provided with a threshold setting portion that sets the threshold, wherein the storage portion may store a correspondence relationship between the incident light level on the imaging device and the SN ratio, for each exposure time.

In the above-described aspect, the sensitivity adjusting portion may be provided with an illuminance calculating portion that calculates, based on the luminance information, an imaging-surface illuminance which is an incident light level on the imaging device per unit time; and a storage portion that stores correspondence relationships between the imaging-surface illuminance of the imaging device and the number of pixels for binning summing, as well as the exposure time, wherein the number of pixels for binning summing and the exposure time may be determined from the correspondence relationship stored in the storage portion by using the imaging-surface illuminance calculated by the illuminance calculating portion.

The above-described aspect may be provided with an illumination light source that emits illumination light to be radiated onto the imaging subject; and a reference-image acquisition portion that acquires a reference image by capturing reflected light coming from the imaging subject due to the illumination light from the illumination light source, wherein the storage portion may store correspondence relationships between the imaging-surface illuminance at the imaging device and the number of pixels for binning summing, as well as the exposure time for each blurring level of the reference image; and the sensitivity adjusting portion may determine the number of pixels for binning summing and the exposure time by using the correspondence relationship selected in accordance with the blurring level calculated based on the luminance information of the reference image acquired by the reference-image acquisition portion.

The above-described aspect may be provided with an illumination light source that emits illumination light to be radiated onto the imaging subject; and a reference-image acquisition portion that acquires a reference image by capturing reflected light coming from the imaging subject due to the illumination light from the illumination light source, wherein the storage portion may store correspondence relationships between the imaging-surface illuminance at the imaging device and the number of pixels for binning summing, as well as the exposure time for each luminance of the reference image; and the sensitivity adjusting portion may determine the number of pixels for binning summing and the exposure time by using the correspondence relationship selected in accordance with the luminance information of the reference image acquired by the reference-image acquisition portion.

The above-described aspect may be provided with a contrast calculating portion that calculates a contrast of the fluorescence image based on the luminance information of the fluorescence image acquired by the fluorescence-image acquisition portion, wherein the threshold setting portion may set the threshold on the basis of the contrast calculated by the contrast calculating portion.

The above-described aspect may be provided with an illumination light source that emits illumination light to be radiated onto the imaging subject; and a reference-image acquisition portion that acquires a reference image by capturing reflected light coming from the imaging subject due to the illumination light from the illumination light source, wherein the threshold setting portion may set the threshold on the basis of the luminance information of the reference image acquired by the reference-image acquisition portion.

The above-described aspect may be provided with a display portion that displays the fluorescence image; and a display-image correcting portion that corrects the brightness of the fluorescence image acquired by the fluorescence-image acquisition portion on the basis of the incident light level calculated by the incident-light-level calculating portion and outputs the image to the display portion.

The above-described aspect may be provided with an attached/detached part that stores identification information and that is attached/detached to change observation conditions; and an identification-information reading portion that reads the identification information stored in the attached/detached part, wherein the sensitivity adjusting portion may store, in the storage portion, a correspondence relationship between the incident light level on the imaging device and the number of pixels for binning summing for each piece of identification information and may also select the correspondence relationship on the basis of the identification information read by the identification-information reading portion.

BRIEF DESCRIPTION OF THE SEVERAL VIEWS OF THE DRAWINGS

FIG. 13 is a diagram showing a table of a correspondence relationship between the contrast and a threshold of the SN ratio, which is stored in a sensitivity setting portion of the fluorescence observation apparatus in FIG. 12.

FIG. 15 is a diagram showing a table of a correspondence relationship between the luminance of a reference image and a threshold of the SN ratio, which is stored in a sensitivity setting portion of the fluorescence observation apparatus in FIG. 14.

FIG. 17 is a diagram showing, for the case in which image blurring is small, a table of a correspondence relationship between the imaging-surface illuminance and a number of pixels for binning summing, which is stored in a sensitivity setting portion of the fluorescence observation apparatus in FIG. 16.

FIG. 18 is a diagram showing, for the case in which image blurring is large, a table of a correspondence relationship between the imaging-surface illuminance and a number of pixels for binning summing, which is stored in the sensitivity setting portion of the fluorescence observation apparatus in FIG. 16.

FIG. 20 is a diagram showing, for the case in which the luminance of a reference image is low, a table of correspondence relationship between the imaging-surface illuminance and a number of pixels for binning summing, which is stored in the sensitivity setting portion of the fluorescence observation apparatus in FIG. 19.

FIG. 21 is a diagram showing, for the case in which the luminance of a reference image is high, a table of a correspondence relationship between the imaging-surface illuminance and a number of pixels for binning summing, which is stored in the sensitivity setting portion of the fluorescence observation apparatus in FIG. 19.

DETAILED DESCRIPTION OF THE INVENTION

A fluorescence observation apparatus 1 according to a first embodiment of the present invention will be described below with reference to the drawings.

Figure 1:
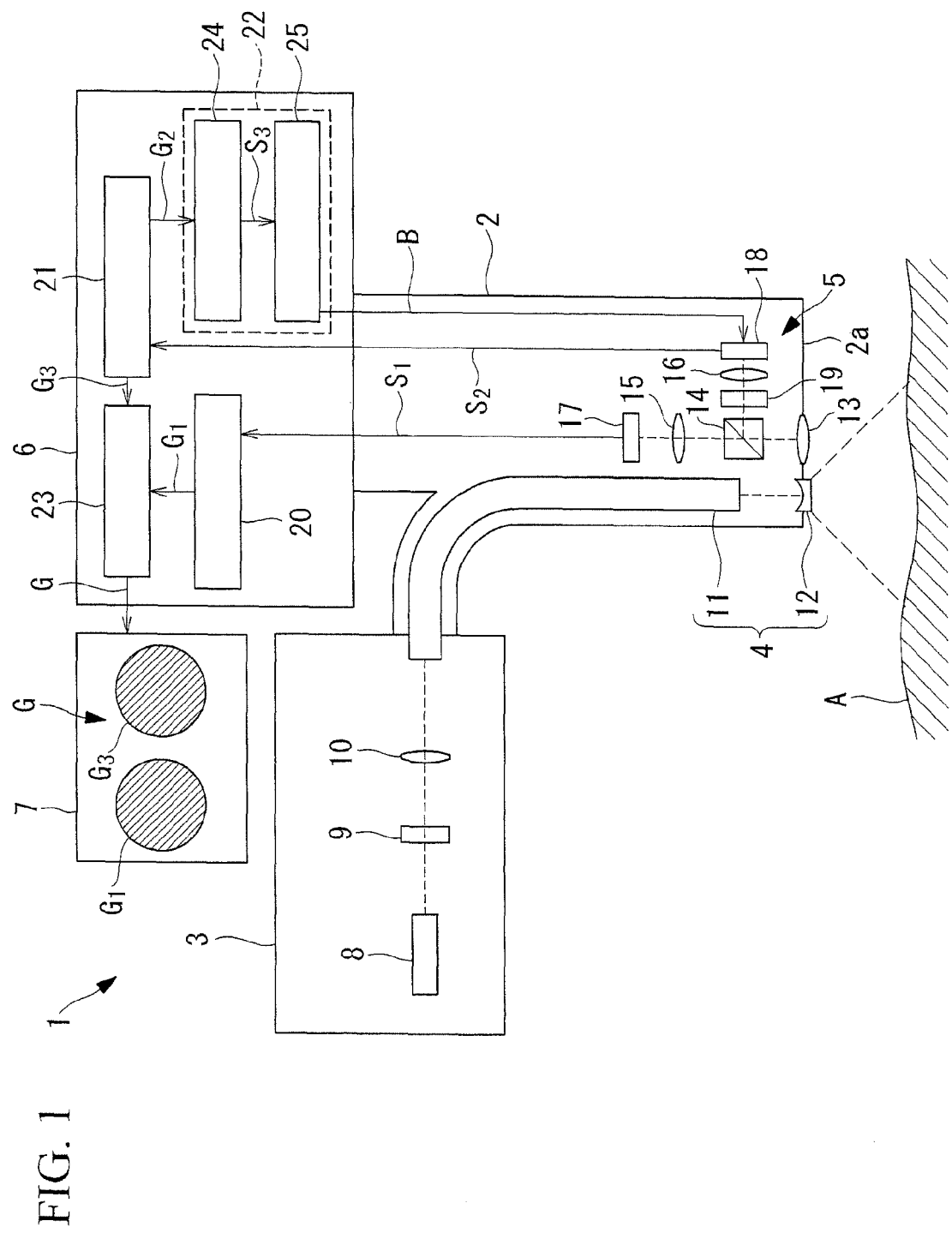
FIG. 1 is an overall configuration diagram showing a fluorescence observation apparatus according to a first embodiment of the present invention.

The fluorescence observation apparatus 1 according to this embodiment is an endoscope apparatus, and, as shown in FIG. 1, it is provided with a long, thin inserted portion 2 that is inserted into a body; a light source (illuminating portion) 3; an illumination unit (illuminating portion) 4 that radiates illumination light and excitation light from the light source 3 toward an observation subject A from the distal end of the inserted portion 2; an imaging unit 5 that is provided at the distal end of the inserted portion 2 and that acquires image information about biological tissue, that is, the observation subject A; an image processing portion 6 that is disposed at the proximal end of the inserted portion 2 and that processes the image information acquired by the imaging unit 5; and a monitor (display portion) 7 that displays an image G processed by the image processing portion 6.

The light source 3 is provided with a xenon lamp 8; a filter 9 that extracts the excitation light and the illumination light (wavelength band 400 to 740 nm) from the illumination light emitted from the xenon lamp 8; and a coupling lens 10 that focuses the excitation light and the illumination light extracted by the filter 9.

The illumination unit 4 is provided with a light-guide fiber 11 that is disposed along nearly the entire length of the inserted portion 2 in the longitudinal direction thereof and that guides the excitation light and the illumination light focused by the coupling lens 10; and an illumination optical system 12 that is provided at the distal end of the inserted portion 2, that spreads the excitation light and the illumination light guided thereto by the light-guide fiber 11, and that radiates them onto the observation subject A facing a distal-end surface 2a of the inserted portion 2.

The imaging unit 5 is provided with an objective lens 13 that collects light returning from a predetermined observation area of the observation subject A; a dichroic mirror (splitting portion) 14 that, of the return light collected by the objective lens 13, reflects light having a wavelength equal to or higher than an excitation wavelength (the excitation light and fluorescence) and allows the illumination light having a shorter wavelength than the excitation wavelength to pass therethrough; two focusing lenses (imaging optical systems) 15 and 16 that individually focus reflected light of the illumination light that has passed through the dichroic mirror 14 and the fluorescence reflected by the dichroic mirror 14; and two imaging devices 17 and 18, such as CMOS devices, that capture images of the fluorescence and the reflected light of the illumination light focused by the focusing lenses 15 and 16. In the figure, reference sign 19 indicates an excitation-light cut filter that blocks the excitation light in the light reflected by the dichroic mirror 14.

The image processing portion 6 is provided with a reference-image generating portion 20 that generates a reference image $G_1$ from reference-image information $S_1$ acquired by the imaging device 17; a fluorescence-image generating portion 21 that generates a fluorescence image $G_2$ from fluorescence-image information $S_2$ acquired by the imaging device 18; a sensitivity adjusting portion 22 that adjusts the sensitivity of the imaging device 17 on the basis of the fluorescence image $G_2$ generated by the fluorescence-image generating portion 21; and an image combining portion 23 that generates an image G by combining a fluorescence image $G_3$ that is acquired in the state in which the sensitivity thereof is adjusted by the sensitivity adjusting portion 22 and the reference image $G_1$ generated by the reference-image generating portion 20.

The sensitivity adjusting portion 22 is provided with an incident-light-level calculating portion 24 that calculates an incident light level $p_{in}$ on the imaging device 18 on the basis of luminance information of the fluorescence image $G_2$ and a sensitivity setting portion 25 (storage portion) that stores a table indicating a correspondence relationship between incident light levels $S_3$ and numbers of pixels B for binning summing; and is configured such that the sensitivity setting portion 25 searches for a number of pixels B for binning summing that corresponds to the incident light level $p_{in}$ calculated by the incident-light-level calculating portion 24 from the table and sets it in the imaging device 18.

The image combining portion 23 combines the image G, for example, so that the reference image $G_1$ and the corrected fluorescence image $G_3$ are displayed on the monitor 7 at the same time in a side-by-side arrangement, and outputs it to the monitor 7.

Here, a method by which the incident-light-level calculating portion 24 calculates the incident light level $p_{in}$ will be described.

When light is incident on an imaging surface of the imaging device 18, at the imaging device 18, the entered light is converted to electron charge in accordance with the quantum efficiency (photon/electron-charge conversion efficiency), and this electron charge is converted to a voltage by an amplifier in accordance with an electron-charge/voltage conversion coefficient. This voltage value is converted to a digital signal in accordance with an A/D conversion coefficient of an A/D converter.

Therefore, a gradation value (luminance information) V, that is, a representative value of a pixel in the fluorescence image $G_2$, is determined by using Expression (1). An average value or a median value of the luminance of all pixels, an average value of the luminance of a region of interest, or an average value of the luminance in the top several percent of a histogram is used as the representative value.

$$V = p_{in} S B \eta C_{I\text{-}V} C_{A\text{-}D} \qquad (1)$$

Here, $p_{in}$ is the incident light level (photon/μm²), S is the imaged pixel area (μm²/pixel), B is the number of pixels for binning summing (pixels), η is the quantum efficiency (electron charge/photon), $C_{I\text{-}V}$ is the electron-charge/voltage conversion coefficient (mV/electron charge), and $C_{A\text{-}D}$ is the A/D conversion coefficient.

From Expression (1), the incident light level $p_{in}$ can be calculated by using Expression (2).

$$p_{in} = V / (S B \eta C_{I\text{-}V} C_{A\text{-}D}) \qquad (2)$$

Next, the relationship between the incident light level $p_{in}$ and an SN ratio S/N will be described. The SN ratio S/N is also dependent on noise characteristics possessed by the imaging device 18.

When a CMOS device is employed as the imaging device 18, the SN ratio S/N can be determined by using Expression (3).

$$S/N = S\eta p_{in}/\sqrt{((S\eta p_{in} + N_d t + N_r^2)/B)} \quad (3)$$

Here, $N_d$ is the dark current per unit time per pixel (electron charge/sec/pixel), $N_r$ is the amount of readout noise (rms electron charge), t is the exposure time (sec), and B is the number of pixels for binning summing.

Figures 2, 3:
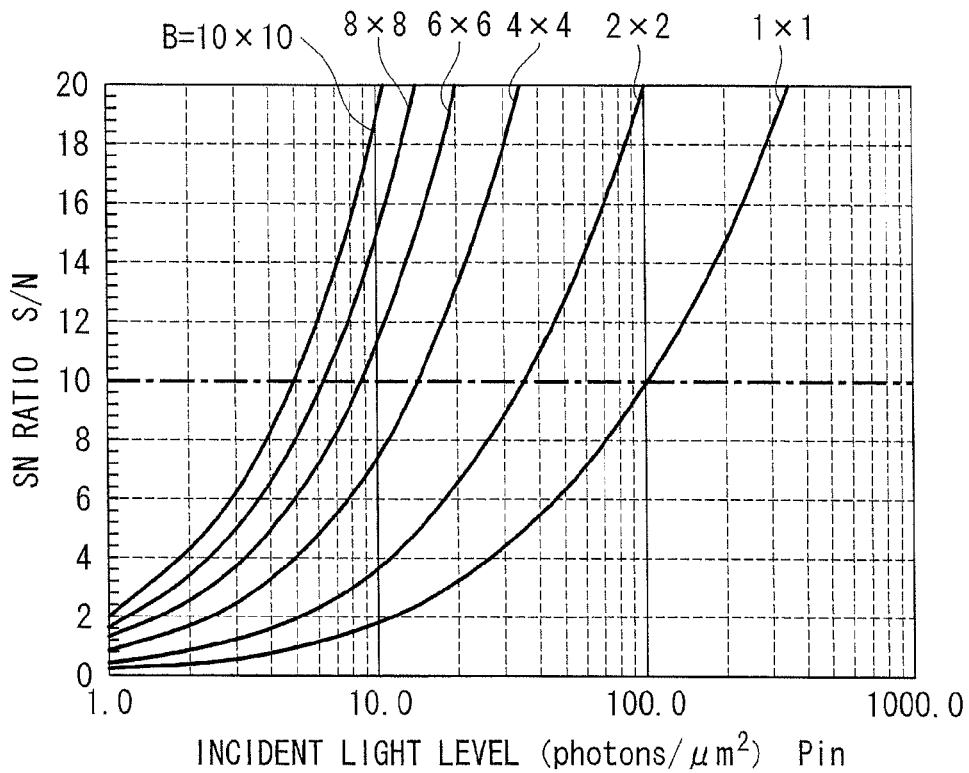
FIG. 2 is a diagram showing a graph of the relationship between the SN ratio of a fluorescence image and an incident light level used in the fluorescence observation apparatus in FIG. 1.
FIG. 3 is a diagram showing a table of the relationship between the incident light level and a number of pixels for binning summing, created on the basis of the graph in FIG. 2.

From Expression (3), the relationship between the incident light level $p_{in}$ and the SN ratio S/N can be represented as in FIG. 2 when the number of pixels B for binning summing is used as a parameter. In FIG. 2, examples of no binning (1×1) to 10×10 are shown as the number of pixels B for binning summing. In this Example, $S \approx 3.0$ μm²/pixel, $\eta \approx 0.4$, $N_d \approx 50$ electron charges/sec/pixel, and $N_r \approx 5.4$ rms electron charges are used as examples. These values should be appropriately changed depending on the imaging device and so forth to be used.

As shown in FIG. 3, the table stored in the sensitivity setting portion 25 of the sensitivity adjusting portion 22 indicates the correspondence relationship between the incident light levels $p_{in}$ and the lowest number of pixels B for binning summing required to achieve an SN ratio S/N equal to or higher than 10 in the graph shown in FIG. 2. In this table, the exposure time t is fixed at, for example, 0.024 sec (24 msec).

The operation of the thus-configured fluorescence observation apparatus 1 according to this embodiment will be described below.

To perform fluorescence observation by using the fluorescence observation apparatus 1 according to this embodiment, the illumination light and the excitation light emitted from the light source 3 are guided to the distal end of the inserted portion 2 via the light-guide fiber 11 and are radiated onto the observation subject A by being spread by the illumination optical system 12. When a fluorescent substance exists in the observation subject A, the fluorescent substance is excited by the excitation light, thus emitting fluorescence. The illumination light is reflected at the surface of the observation subject A.

The fluorescence generated inside the observation subject A and the reflected light of the illumination light reflected at the surface of the observation subject A are collected by the objective lens 13, are subsequently split into two by the dichroic mirror 14, and are captured by the two imaging devices 17 and 18. Because the two types of light collected by the single objective lens 13 are split by the dichroic mirror 14, it is possible to observe the same area of the observation subject A by using two types of observation methods.

The reference-image information $S_1$ acquired via image-capturing with by the imaging device 17 is transmitted to the reference-image generating portion 20 of the image processing portion 6, and thus, the reference image $G_1$ is generated. On the other hand, the fluorescence-image information $S_2$ acquired via image-capturing with the imaging device 18 is transmitted to the fluorescence-image generating portion 21 of the image processing portion 6, and thus, the fluorescence image $G_2$ is generated.

Figure 4:
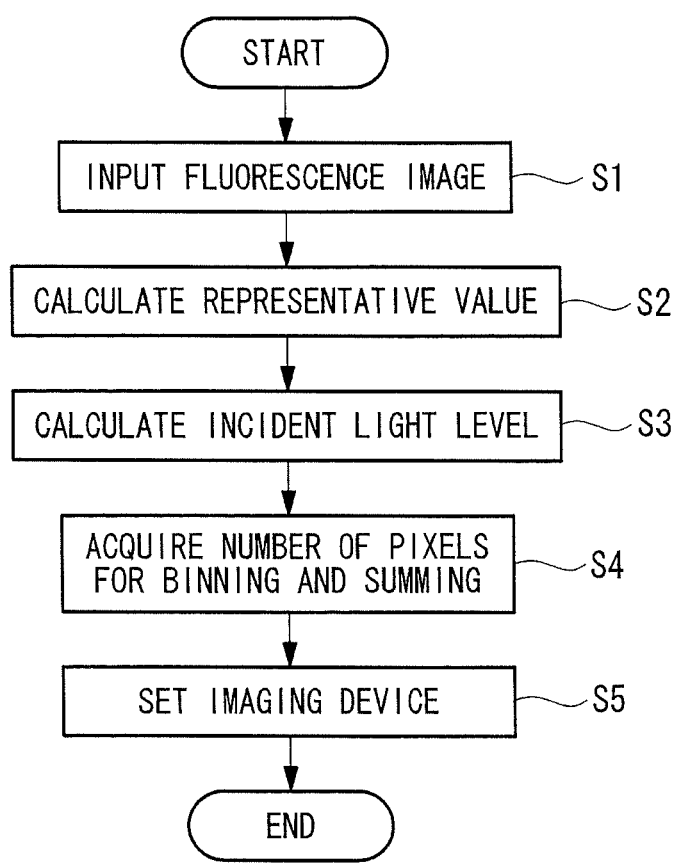
FIG. 4 is a flowchart showing the procedure for setting the sensitivity of an imaging device in the fluorescence observation apparatus in FIG. 1.

As shown in FIG. 4, the generated fluorescence image $G_2$ is transmitted to the sensitivity adjusting portion 22 (Step S1), and the representative value thereof is determined (Step S2). Then, the determined representative value is input to the incident-light-level calculating portion 24, where it is applied to Expression (2), and thus, the incident light level $p_{in}$ is calculated (Step S3). By inputting the calculated incident light level $p_{in}$ to the sensitivity setting portion 25, a number of pixels B for binning summing that corresponds to the incident light level $p_{in}$ is output from the sensitivity setting portion 25 and is set in the imaging device 18 (Step S5).

By doing so, the imaging device 18 in which a new number of pixels B for binning summing is set acquires new fluorescence-image information $S_2$, and the fluorescence image $G_3$ generated by the fluorescence-image generating portion 21 is displayed on the monitor 7 in the form of the combined image G by being combined with the reference image $G_1$ at the image combining portion 23.

In this case, with the fluorescence observation apparatus 1 according to this embodiment, because the number of pixels B for binning summing is determined from the table stored in the sensitivity setting portion 25 in accordance with the incident light level $p_{in}$ determined based on the luminance information of the fluorescence image $G_2$, there is an advantage in that the lowest number of pixels B for binning summing with which the SN ratio S/N equal to or higher than the threshold is achieved can be set in the imaging device 18, and the resolution can be enhanced while preventing deterioration of the image quality.

Moreover, of the number of pixels for binning summing with which noise can be suppressed, the lowest number of pixels for binning summing with which the resolution can be maintained as much as possible is selected, thereby making it possible to perform clear fluorescence observation at an appropriate sensitivity.

Specifically, because the incident light level $p_{in}$, that is, the number of photons that has entered per unit area, is used as the reference, the signal value for calculating the SN ratio S/N does not change even if the number of pixels B for binning summing is changed. When the sensitivity is adjusted by using the brightnesses of the images as the reference, as has been done in the related art, the signal value sometimes changes even if the brightnesses of the images are the same, and thus, a suitable threshold cannot be set; however, with this embodiment, a suitable threshold can be set without being affected by the number of pixels B for binning summing.

With this embodiment, even if the number of pixels B for binning summing is set to be the highest (10×10), the SN ratio S/N becomes less than 10 when the incident light level $p_{in}$ calculated by the incident-light-level calculating portion 24 is less than 5 photons/μm²; therefore, in such a case, a warning may be displayed on the monitor 7. In this case, by making an improvement, such as reducing the observation distance or the like, observation can be performed with an SN ratio S/N equal to or higher than 10.

The highest number of pixels B for binning summing is not limited to 10×10, and it may be higher or lower.

The threshold of the SN ratio S/N may be set at a value other than 10, depending on the performance or the like of fluorescent agents to be used. For example, when using a fluorescent agent that has high disease specificity and exhibits a large difference in terms of the generated amount of fluorescence in comparison with normal tissue, the threshold may be set to be relatively low. By doing so, it is possible to perform fluorescence observation at higher resolution and higher sensitivity. Moreover, it is possible to perform appropriate fluorescence observation by setting a suitable threshold in accordance with the performance of fluorescent agents to be used and the application.

Next, a fluorescence observation apparatus 30 according to a second embodiment of the present invention will be described below with reference to the drawings.

In describing this embodiment, the same reference signs are assigned to portions having common configurations with the fluorescence observation apparatus 1 according to the first embodiment described above, and descriptions thereof will be omitted.

The fluorescence observation apparatus 30 according to this embodiment differs from the fluorescence observation apparatus 1 according to the first embodiment in that, the sensitivity adjusting portion 22 adjusts not only the number of pixels B for binning summing but also the exposure time t.

Figure 5:
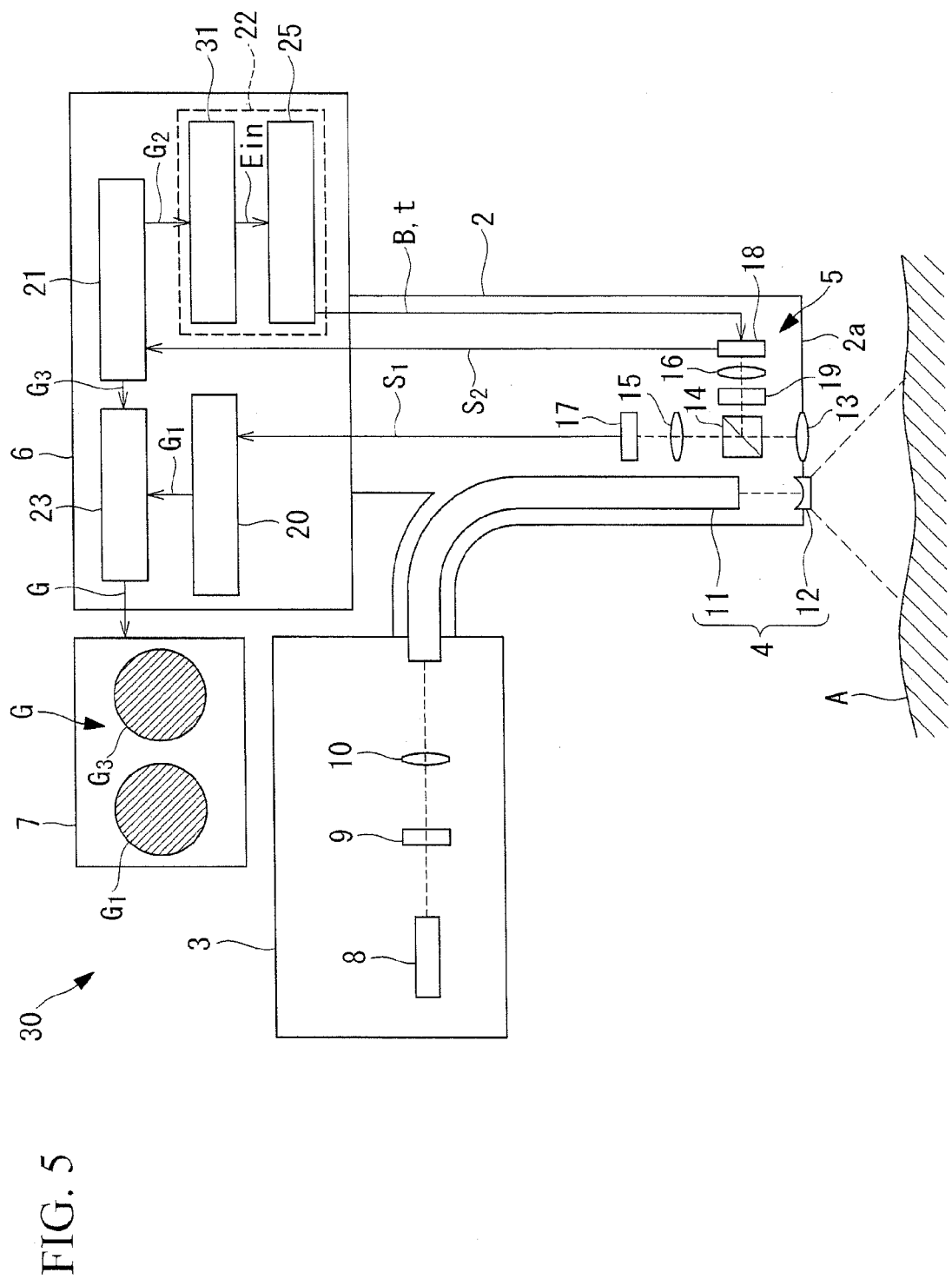
FIG. 5 is an overall configuration diagram showing a fluorescence observation apparatus according to a second embodiment of the present invention.

Specifically, as shown in FIG. 5, the sensitivity adjusting portion 22 of the fluorescence observation apparatus 30 according to this embodiment is provided with an illuminance calculating portion 31 that calculates an imaging-surface illuminance $E_{in}$ at the imaging surface of the imaging device 18 on the basis of the luminance information of the fluorescence image $G_2$; and the sensitivity setting portion (storage portion) 25 that stores a table that indicates correspondence relationships between the imaging-surface illuminance $E_{in}$ and the number of pixels B for binning summing, as well as the exposure time t.

The imaging-surface illuminance $E_{in}$ is an incident light level per unit time at the imaging surface, and it can be calculated by using Expression (4).

$$E_{in} = V/(tSB\eta C_{I\text{-}V} C_{A\text{-}D}) \quad (4)$$

Accordingly, the sensitivity setting portion 25 searches for the number of pixels B for binning summing and the exposure time t that correspond to the imaging-surface illuminance $E_{in}$ calculated by the illuminance calculating portion 31 from the table and sets them in the imaging device 18.

Here, because $$p_{in} = E_{in} t \quad (5)$$

from Expression (3) and Expression (5), the relationship between the SN ratio S/N and the imaging-surface illuminance $E_{in}$ can be expressed as in Expression (6).

$$S/N = S\eta E_{in} t / \sqrt{((S\eta E_{in} t + N_d t + N_r^2)/B)} \quad (6)$$

Figures 6, 7:
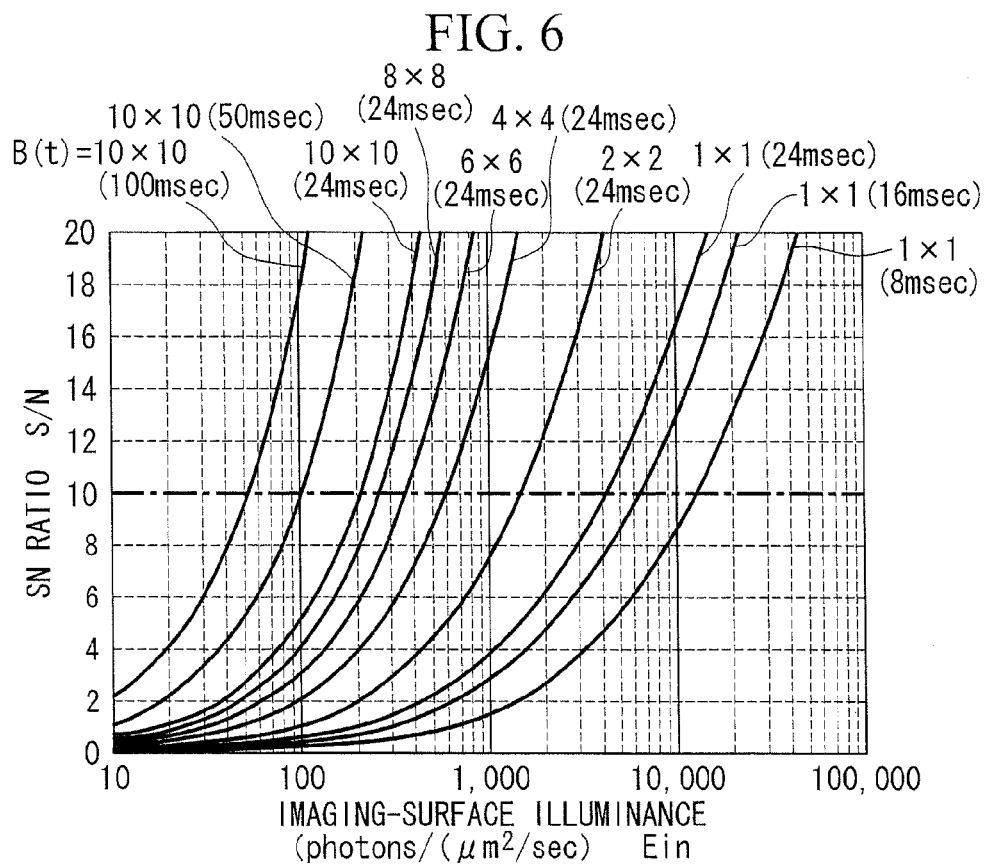
FIG. 6 is a diagram showing a graph of the relationship between the SN ratio of a fluorescence image and an imaging-surface illuminance used in the fluorescence observation apparatus in FIG. 5.
FIG. 7 is a diagram showing a table of the relationship between the imaging-surface illuminance and the number of pixels for binning summing, as well as the exposure time, created on the basis of the graph in FIG. 6.

Specifically, as shown in FIG. 6, the SN ratio S/N can be expressed as a function of the imaging-surface illuminance $E_{in}$ that includes the number of pixels B for binning summing and the exposure time t as parameters.

Then, the table for obtaining the number of pixels B for binning summing and the exposure time t based on the imaging-surface illuminance $E_{in}$ is such that the number of pixels B for binning summing is adjusted by using the exposure time of 24 msec in the table in the first embodiment shown in FIG. 7 as a standard, and the exposure time t is increased or decreased when the number of pixels B for binning summing reaches the highest or lowest value. S, η, Nd, and $N_r$ used here take the same values as in the first embodiment.

Figure 8:
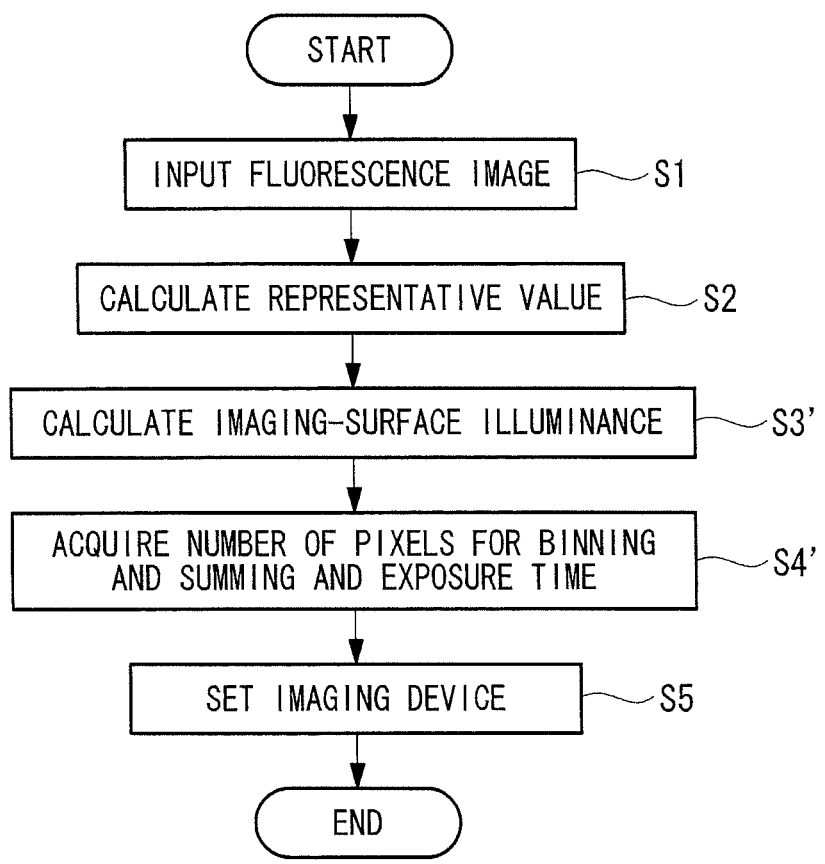
FIG. 8 is a flowchart showing the procedure for setting the sensitivity of an imaging device in the fluorescence observation apparatus in FIG. 5.

As shown in FIG. 8, with the thus-configured fluorescence observation apparatus 30 according to this embodiment, the imaging-surface illuminance $E_{in}$ is determined based on the luminance information of the fluorescence image $G_2$ (Step S3'), and the number of pixels B for binning summing and the exposure time t are determined from the table stored in the sensitivity setting portion 25 in accordance with that imaging-surface illuminance $E_{in}$ (Step S4'). When the imaging-surface illuminance $E_{in}$ is equal to or less than 100 to 250 photons/sec/μm², 100 to 24 msec is selected as the exposure time t in a state in which the number of pixels B for binning summing is fixed at 10×10.

When the imaging-surface illuminance $E_{in}$ is 208 to 4330 photons/sec/μm², the number of pixels B for binning summing is selected between 10×10 and 1×1 in the state in which the exposure time t is fixed at 24 msec. Furthermore, when the imaging-surface illuminance $E_{in}$ is equal to or higher than 6500 photons/sec/μm², the exposure time t is selected between 24 and 8 msec in the state in which the number of pixels B for binning summing is fixed at 1×1.

By doing so, it is possible to ensure that the SN ratio S/N is equal to or higher than 10 by increasing the exposure time t, even when observing weak fluorescence whose incident light level $p_{in}$ is less than 5 photons/μm⁻². In a region in which the imaging-surface illuminance $E_{in}$ is high (4330 photons/sec/μm² or higher), although a sufficiently high SN ratio S/N can be obtained even if the number of pixels B for binning summing is set to be the lowest, that is, 1×1, there is an advantage in that the image-blurring suppression effect can be increased by setting a lower exposure time t with an increase in the imaging-surface illuminance $E_{in}$.

Moreover, of the exposure times with which noise can be suppressed, the lowest exposure time with which the resolution can be maintained as much as possible is selected, thereby making it possible to perform clear fluorescence observation at an appropriate sensitivity. Accordingly, it is possible to perform sensitivity adjustment in a greater range where sufficient adjustment cannot be achieved by adjusting only the number of pixels for binning summing.

Next, a fluorescence observation apparatus 40 according to a third embodiment of the present invention will be described with reference to the drawings.

In describing this embodiment, the same reference signs are assigned to portions having common configurations with the fluorescence observation apparatus 1 according to the first embodiment, and descriptions thereof will be omitted.

Figure 9:
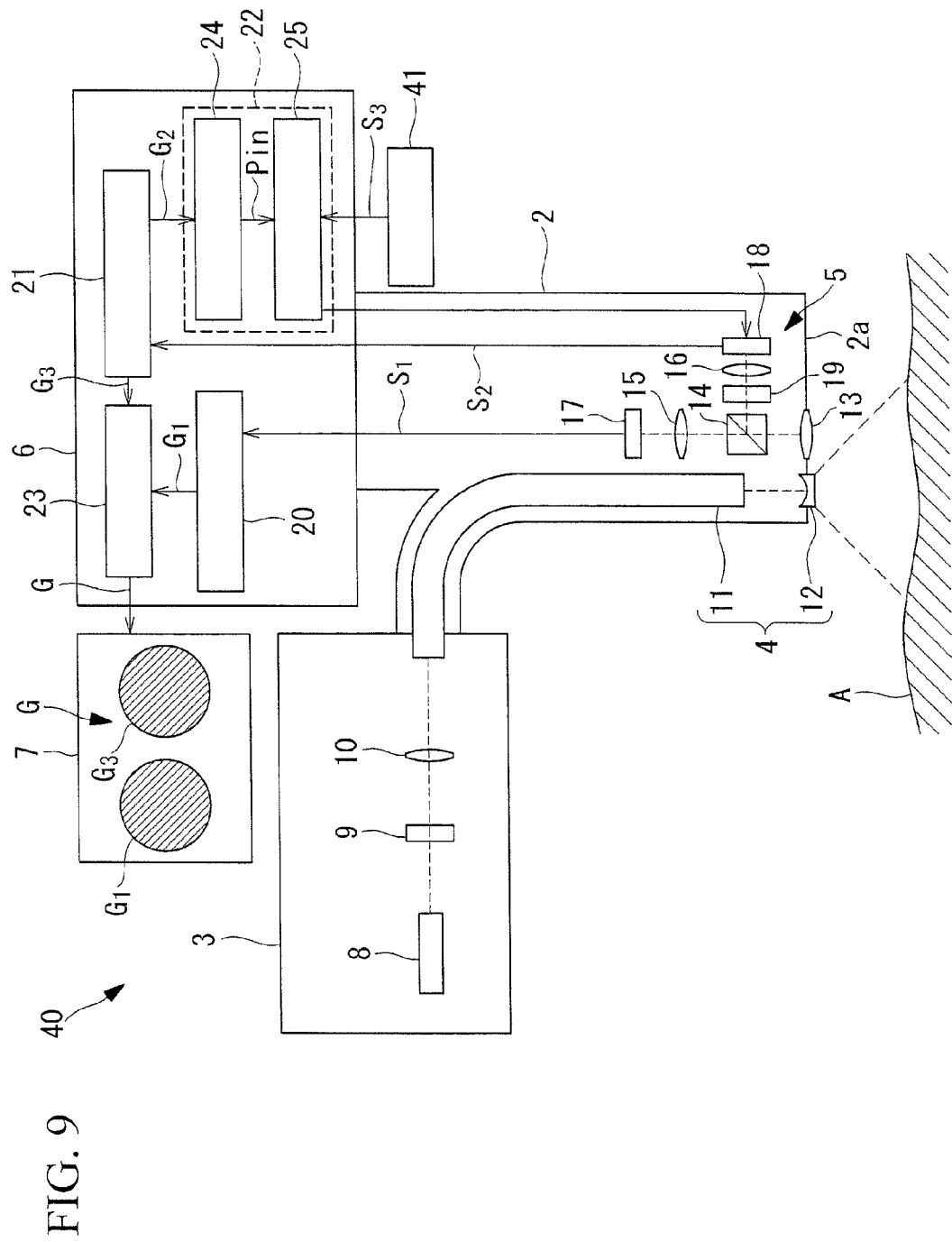
FIG. 9 is an overall configuration diagram showing a fluorescence observation apparatus according to a third embodiment of the present invention.

As shown in FIG. 9, a fluorescence observation apparatus 40 according to this embodiment differs from the fluorescence observation apparatus 1 according to the first embodiment described above in that it is provided with a threshold inputting portion (threshold setting portion) 41 that allows external input of a threshold $S_3$ for determining the number of pixels B for binning summing at the sensitivity setting portion 25.

The threshold inputting portion 41 is, for example, a switching lever, a button, or the like, and is configured so that one of 6, 10, and 15 can be selected as the threshold $S_3$ for the SN ratio S/N.

Figures 10, 11:
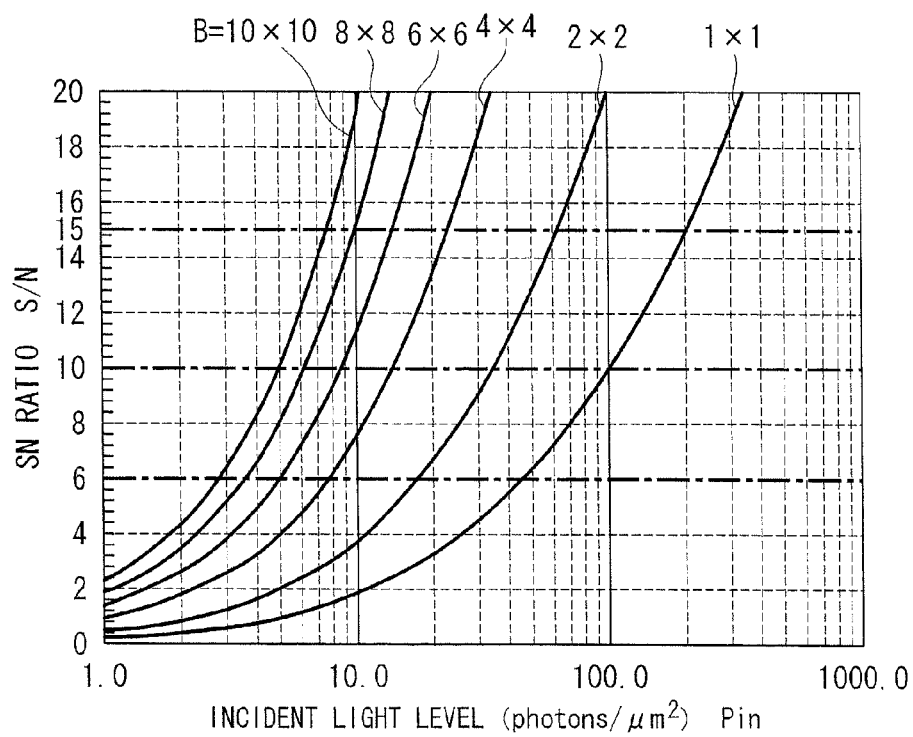
FIG. 10 is a diagram showing an example of a table provided in a sensitivity setting portion of the fluorescence observation apparatus in FIG. 9.
FIG. 11 is a diagram showing an example of a graph provided in the sensitivity setting portion of the fluorescence observation apparatus in FIG. 9.

The table shown in FIG. 10 is stored in the sensitivity setting portion 25. On the basis of the threshold $S_3$ input from the threshold inputting portion 41 and the incident light level $p_{in}$ calculated by the incident-light-level calculating portion 24, the sensitivity setting portion 25 selects the number of pixels B for binning summing from the table and sets it in the imaging device 18.

With the thus-configured fluorescence observation apparatus 40 according to this embodiment, it is possible to set a suitable threshold $S_3$ for the SN ratio S/N in accordance with the performance of reagents and the application. For example, because the SN ratio S/N required for the imaging device 18 can be low when a high-contrast fluorescent agent is used, by setting a low threshold $S_3$, the number of pixels B for binning summing can be set to be low even if the incident light level $p_{in}$ is low, and thus, deterioration of the resolution and the influence of imaging blurring can be minimized.

In contrast, by increasing the threshold for the SN ratio S/N, in an application in which the observation distance is assumed to be large, such as observing an abdominal cavity by using a rigid scope or observing the interior of a stomach by using a flexible scope, a portion to be observed appears relatively small, which may possibly cause deterioration of the visibility, an advantage is afforded in that a sufficient sensitivity for ensuring the visibility can be obtained.

In this embodiment, the number of pixels B for binning summing stored in the table is selected in accordance with the threshold $S_3$ input from the threshold inputting portion 41. Instead of this, the sensitivity setting portion 25 may store a graph shown in FIG. 11 that indicates the relationship between the SN ratio S/N and the incident light level $p_{in}$ for each number of pixels B for binning summing, and, each time the threshold $S_3$ is input, the sensitivity setting portion 25 may use the input threshold $S_3$ to create, based on the stored graph, a table in which the lowest number of pixels B for binning summing with which an SN ratio S/N equal to or higher than that threshold $S_3$ can be achieved is selected. In FIG. 11, lines indicating 6, 10, and 15 are shown as examples of the threshold $S_3$ for the SN ratio S/N.

By doing so, an advantage is afforded in that it is possible to freely set the threshold $S_3$ for the SN ratio S/N independent of the values stored in advance, making it possible to perform finer sensitivity adjustment.

The input threshold $S_3$ is used to select the lowest number of pixels B for binning summing with which an SN ratio S/N equal to or higher than that threshold $S_3$ can be achieved from the stored table or graph; however, in addition to this, the number of pixels B for binning summing and the exposure time t may be adjusted, as in the second embodiment. An operator may input the threshold $S_3$ for the SN ratio S/N before starting observation depending on the usage, or he/she may input it during observation depending on the circumstances.

Figure 12:
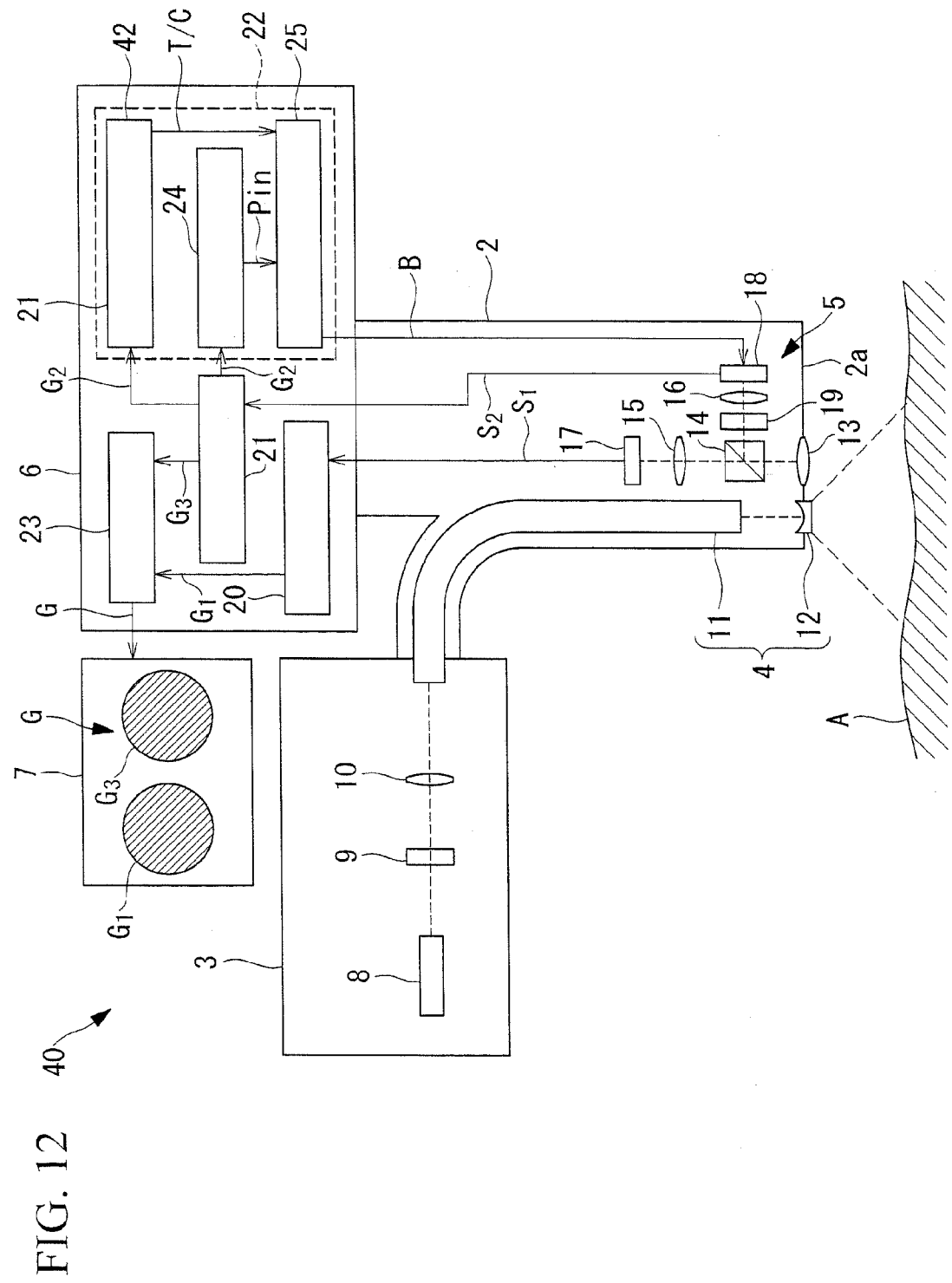
FIG. 12 is an overall configuration diagram showing a first modification of the fluorescence observation apparatus in FIG. 9.

In this embodiment, the threshold $S_3$ input from the threshold inputting portion 41 is used; alternatively, however, a contrast calculating portion 42 that calculates the contrast of an image from the fluorescence image generated by the fluorescence-image generating portion may be provided, as shown in FIG. 12, and the threshold $S_3$ for the SN ratio S/N may be set on the basis of a contrast T/C calculated by the contrast calculating portion 42.

In this case, a table in which the contrast T/C is associated with the threshold $S_3$ should be stored in the sensitivity setting portion 25.

The contrast calculating portion 42 should be configured such that, for example, a histogram of the fluorescence image $G_2$ is generated, and the contrast is calculated in the form of a ratio T/C of an average value C for all gradation values in the histogram and an average value T for the top 5% of the histogram.

As shown in FIG. 13, it is preferable that the table be a table with which the threshold $S_3$ for the SN ratio S/N is set to be low when the contrast T/C of the fluorescent agent to be used is high, and the threshold for the SN ratio S/N is set to be high when the contrast T/C thereof is low. Because the threshold $S_3$ for the SN ratio S/N is set on the basis of an actually obtained fluorescence image $G_2$, it is possible to set a more suitable threshold as compared with the case in which it is manually input.

Moreover, an appropriate threshold is automatically set by using the contrast calculated by the contrast calculating portion based on the acquired fluorescence image, thus automatically making it possible to perform observation at a more appropriate sensitivity without causing deterioration of the image quality of the fluorescence image, even if the observation conditions fluctuate.

Although the average value T for the top 5% of the histogram is used for the contrast T/C, it is not limited thereto, and, for example, in an application for observing a large diseased portion, for example, when observing a colorectal polyp or the like, the average value T of, for example, the top 10% of the histogram may be used because the proportion of a high-luminance region in the fluorescence image $G_2$ is likely to be high.

Instead of setting the threshold $S_3$ for the SN ratio S/N based on the contrast T/C of the fluorescence image $G_2$, the threshold $S_3$ for the SN ratio S/N may be set based on the luminance value of the reference image $G_1$.

Figure 14:
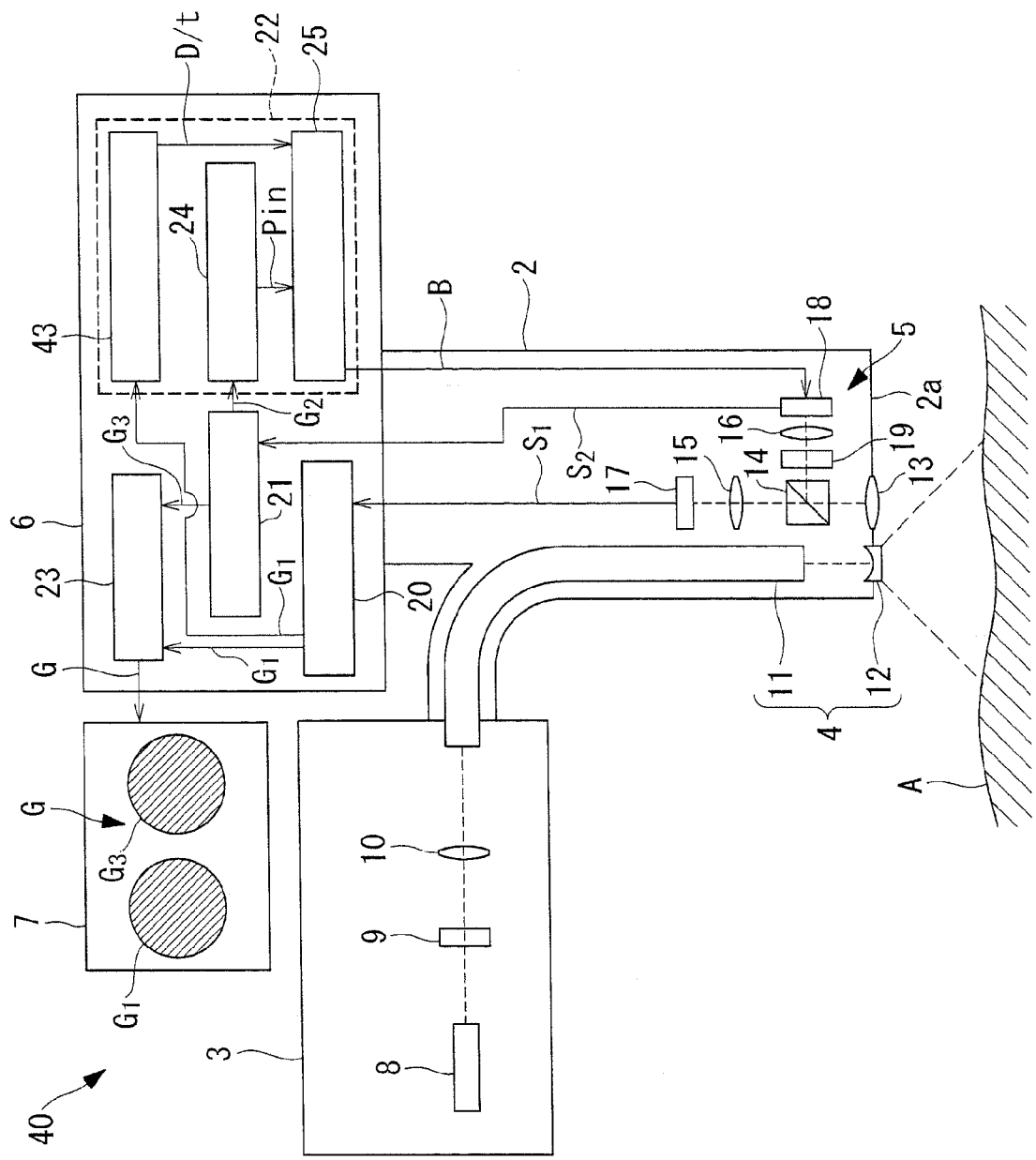
FIG. 14 is an overall configuration diagram showing a second modification of the fluorescence observation apparatus in FIG. 9.

In this case, as shown in FIG. 14, a luminance calculating portion 43 that calculates a luminance D/t of the reference image $G_1$ by dividing a representative value D, such as an average value or the like of the luminance values of the reference image $G_1$ generated by the reference-image generating portion 20, by the exposure time t should be provided, and a table in which the luminance D/t of the reference image $G_1$ is associated with the threshold $S_3$ should be stored in the sensitivity setting portion 25.

As shown in FIG. 15, the table should be a table such that the threshold $S_3$ for the SN ratio S/N is preferably set to be relatively high in order to enhance the visibility of the observation subject A in an application in which the observation distance is large, that is, when the luminance D/t of the reference image $G_1$ is low, and the threshold $S_3$ for the SN ratio S/N is set to be relatively low in an application in which the observation distance is small, that is, when the luminance D/t of the reference image $G_1$ is high.

In contrast, because the portion to be observed is displayed so as to appear large when the observation distance is small, a deterioration in the resolution and the occurrence of image blurring are tolerated to some extent. In this case, the threshold $S_3$ for the SN ratio S/N may be set to be relatively high so that the number of pixels B for binning summing will be relatively high.

Because the portion to be observed is displayed so as to appear small when the observation distance is large, the deterioration of the resolution and the image blurring tend to have a large influence. Therefore, in this case, the threshold $S_3$ for the SN ratio S/N may be set to be relatively low so that an excessively high exposure time t and an excessively large number of pixels B for binning summing are avoided.

Values of the luminance D/t in FIG. 15 are example values in which the luminance values are expressed in 12-bit gradation and the exposure time is expressed by a unit based on seconds. In other words, if D/t is 100,000 when the exposure time is 24 msec, the gradation value is 2400.

Figure 16:
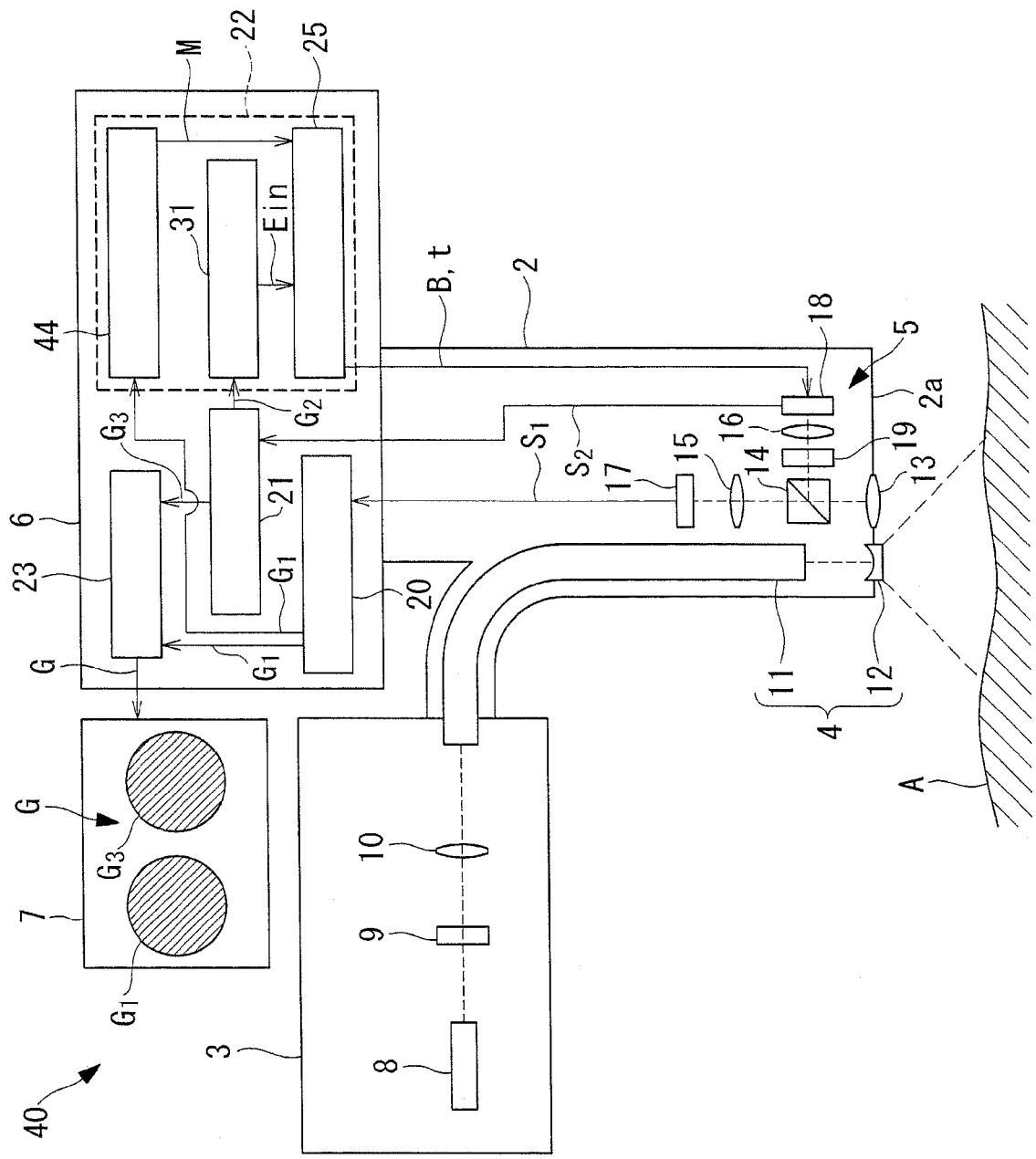
FIG. 16 is an overall configuration diagram showing a third modification of the fluorescence observation apparatus in FIG. 9.

As shown in FIG. 16, an image-blurring calculating portion 44 that calculates image-blurring M based on the reference image $G_1$ generated by the reference-image generating portion 20 may be provided, and the sensitivity setting portion 25 may select a table in which the imaging-surface illuminance $E_{in}$ is associated with the exposure time t and the number of pixels B for binning summing depending on the magnitude of the calculated image-blurring M. The image blurring M can be calculated by, for example, calculating a blurring level by using a known technique and by converting that blurring level into a numerical value.

The sensitivity setting portion 25 compares the image-blurring M transmitted thereto from the image-blurring calculating portion 44 with predetermined thresholds M1 and M2, and separately selects a table for three cases, M<M1, M1<M<M2, and M2<M. An example table for the case in which M<M1 is shown in FIG. 17, an example table for the case in which M1<M<M2 is shown in FIG. 7, and an example table for the case in which M2<M is shown in FIG. 18.

The table in FIG. 17 is for the smallest image blurring M, with which high-resolution observation is performed by giving priority to increasing the exposure time t while keeping the number of pixels B for binning summing low. The table in FIG. 7 is for intermediate image blurring M, in which the number of pixels B for binning summing is changed by setting the exposure t at the standard value of 24 msec. The table in FIG. 18 is for the largest image blurring M, with which the image blurring M is suppressed to enhance the visibility by giving priority to decreasing the exposure time t. Accordingly, it is possible to perform sensitivity adjustment that is more appropriate for the observation situation. The number of pixels for binning summing is adjusted by giving priority to reducing the exposure time when the blurring level is high, and the number of pixels for binning summing is adjusted by giving priority to increasing the exposure time when the image blurring is small, thereby making it possible to perform high-resolution fluorescence observation by reducing the number of pixels for binning summing.

Figure 19:
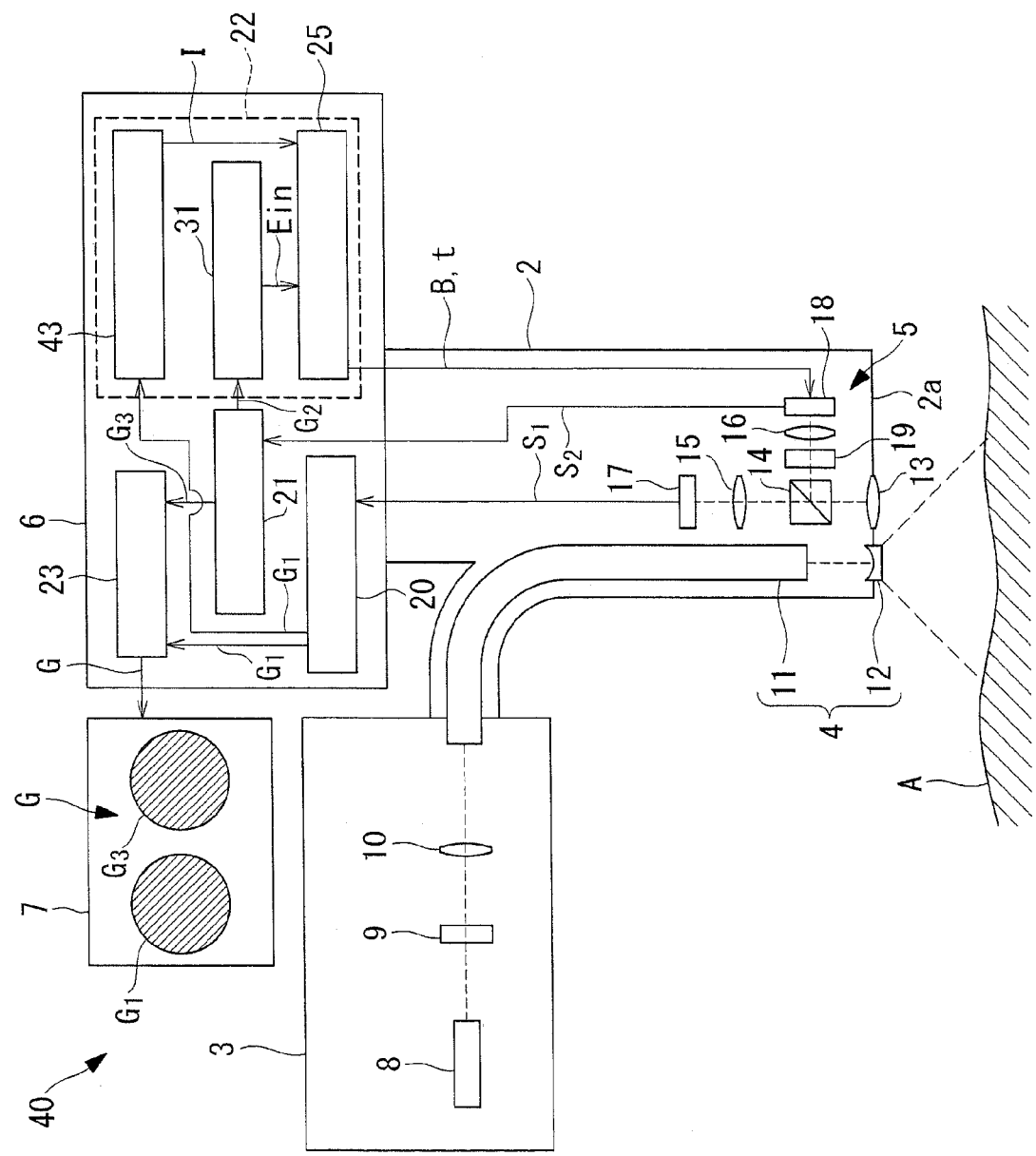
FIG. 19 is an overall configuration diagram showing a fourth modification of the fluorescence observation apparatus in FIG. 9.

As shown in FIG. 19, instead of the image-blurring calculating portion 44, a luminance calculating portion 43 that calculates a luminance I of the reference image $G_1$ generated by the reference-image generating portion 20 may be provided, and the sensitivity setting portion 25 may select a table in which the imaging-surface illuminance $E_{in}$ is associated with the exposure time t and the number of pixels B for binning summing depending on the magnitude of the calculated luminance I of the reference image $G_1$.

The sensitivity setting portion 25 compares the luminance I of the reference image $G_1$ transmitted thereto from the luminance calculating portion 43 with predetermined thresholds I1 and I2, and separately selects a table for three cases, I<I1, I1<I<I2, and I2<I. An example table for the case in which I<I1 is shown in FIG. 20, an example table for the case in which I1<I<I2 is shown in FIG. 7, and an example table for the case in which I2<I is shown in FIG. 21.

The table in FIG. 20 is for the smallest luminance I of reference image $G_1$, with which high-resolution observation is performed by giving priority to increasing the exposure time t while keeping the number of pixels B for binning summing low. The table in FIG. 7 is for intermediate luminance I, in which the number of pixels B for binning summing is changed by setting the exposure t to the standard value of 24 msec. The table in FIG. 21 is for the largest luminance I, with which the image blurring is suppressed to enhance the visibility by giving priority to decreasing the exposure time t.

Accordingly, it is possible to perform sensitivity adjustment that is more appropriate for the observation situation. Because a low luminance I means that the observation distance is large and the size of the diseased portion in an image is decreased, a high-resolution imaging is required. Therefore, this is an effective method for usages in which high resolution is required, including, in particular, when observing a small diseased portion, like a peritoneal metastasis lesion, and a usage in which the observation distance is relatively large, as in abdominal-cavity endoscopy, as well as when observing the interior of the stomach.

Moreover, when the luminance of the reference image is high, the observation distance is small, and thus, the observation subject appears relatively large in the image. Therefore, because the observation subject is visually recognizable in a clear manner even if the resolution is slightly deteriorated, image blurring can be reduced by keeping the exposure time low by setting the number of pixels for binning summing to be relatively high. In contrast, when the luminance of the reference image is low, the observation distance is large, and thus the observation subject appears relatively small in the image. Therefore, the resolution can be increased by setting the number of pixels for binning summing to be relatively low.

In the individual embodiments described above, because the number of pixels B for binning summing and the exposure time t are adjusted by using the SN ratio S/N as a reference, the brightness of the fluorescence image $G_3$ displayed on the monitor 7 sometimes fluctuates.

Figure 22:
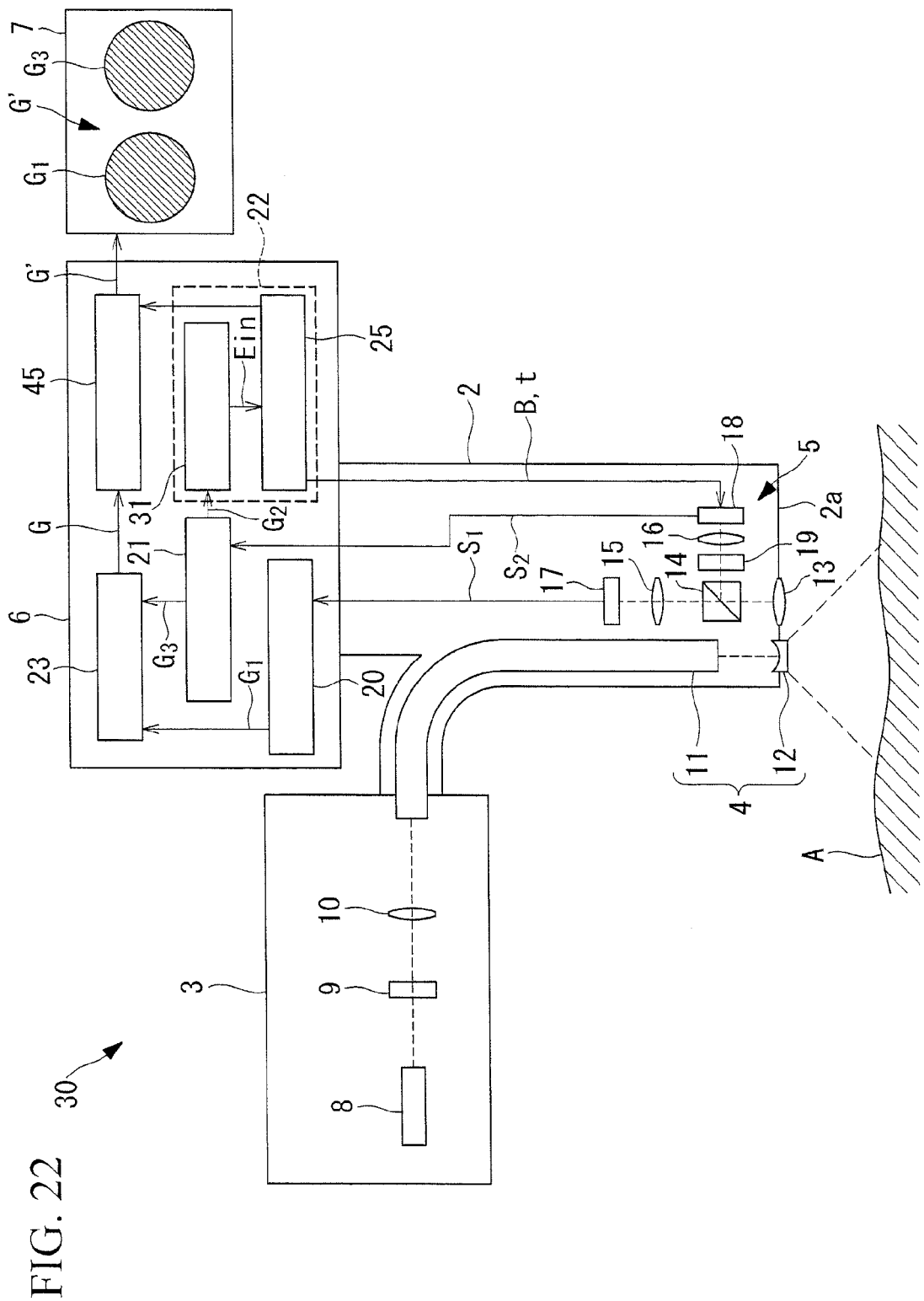
FIG. 22 is an overall configuration diagram showing a modification of the fluorescence observation apparatus in FIG. 5.

To cope with this, as shown in FIG. 22, a display correcting portion 45 may be provided, which performs correction by multiplying the gradation value of the fluorescence image $G_3$ generated by the fluorescence-image generating portion 21 by a conversion factor $C_{raw\text{-}display}$ given by Expression (7) below.

$$C_{raw\text{-}display} = B_{max} t_{max} / Bt \qquad (7)$$

Here, $B_{max}$ is an upper-limit value of the number of pixels B for binning summing, and $t_{max}$ is an upper-limit value of the exposure time t.

By doing so, an advantage is afforded in that it is possible to provide the operator with quantitative information while maintaining the sensitivity by avoiding a situation in which the fluorescence is displayed on the monitor 7 with a brightness differing from the actual brightness due to the sensitivity adjustment.

Figure 23:
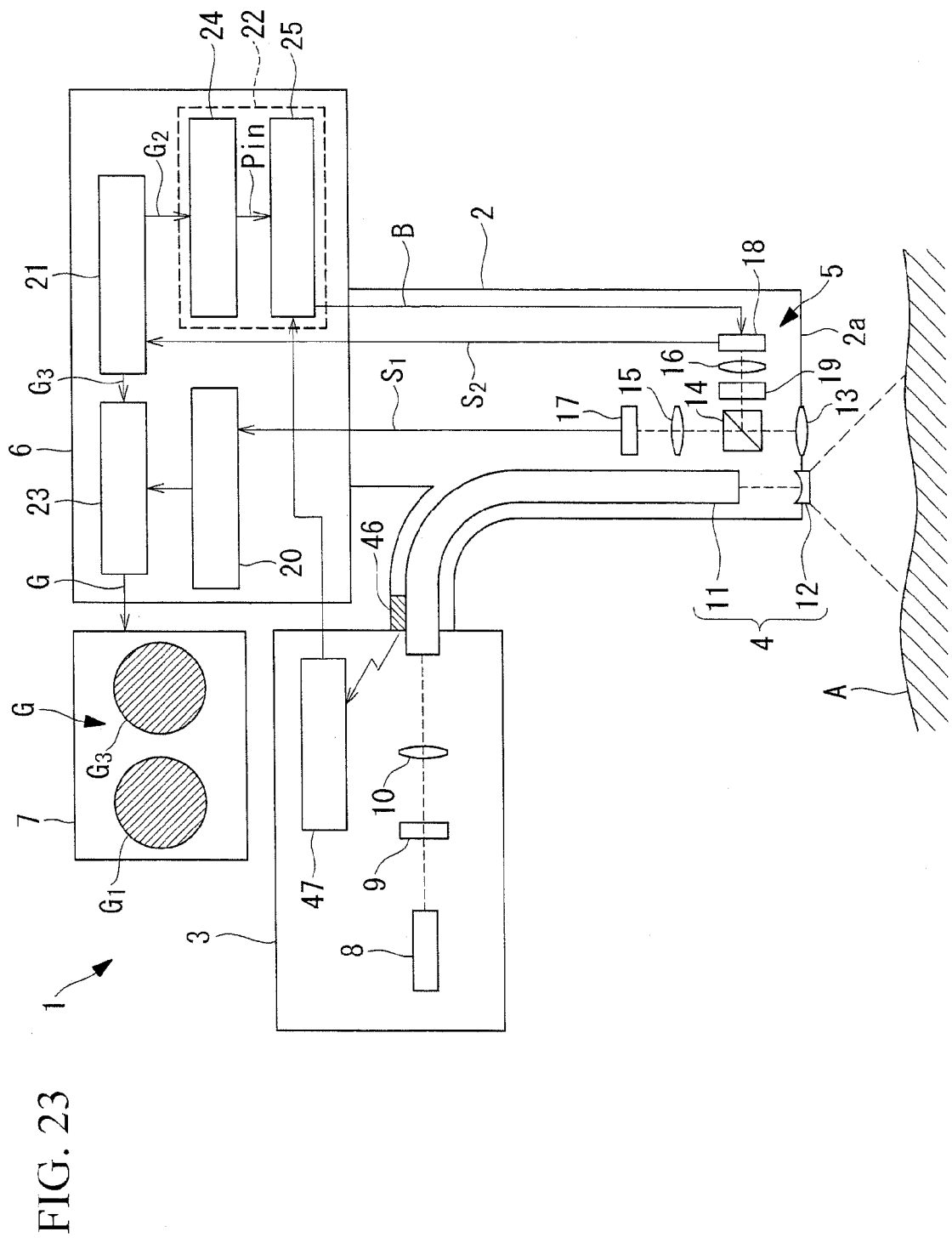
FIG. 23 is an overall configuration diagram showing a modification of the fluorescence observation apparatus in FIG. 1.

As shown in FIG. 23, in this embodiment, an IC chip 46 that stores identification information may be attached to the inserted portion 2 that is attached and detached to change the observation conditions, and the light source 3 may be provided with an IC reader 47 that reads the identification information in the IC chip 46 of the attached inserted portion 2. Then, the sensitivity setting portion 25 may store information indicating a correspondence relationship between the incident light level $p_{in}$ (or the imaging-surface illuminance) and a suitable number of pixels B for binning summing or the exposure time t for each piece of identification information for the inserted portion 2.

By doings so, when the inserted portion 2 is exchanged, the identification information in the IC chip 46 provided in the inserted portion 2 is read by the IC reader 47 and is transmitted to the sensitivity setting portion 25. Because the sensitivity setting portion 25 automatically selects the number of pixels B for binning summing and/or the exposure time t that correspond to the identification information of that inserted portion 2, it is possible to perform observation at an appropriate sensitivity for the observation conditions.

Although CMOS devices are employed as the imaging devices 17 and 18 in this embodiment, alternatively, CCDs may be employed.

When employing the CCDs, Expression (8) should be used instead of Expression (3).

$$S/N = S\eta p_{in}/\sqrt{((S\eta p_{in} + N_d t + N_r^2/B)/B)} \qquad (8)$$

The present invention affords an advantage in that observation can be performed at a more appropriate sensitivity without causing deterioration of the image quality.

What is claim is:

1. A fluorescence observation apparatus comprising:
an excitation light source that emits excitation light to be radiated onto an imaging subject;
a fluorescence-image acquisition portion that is provided with an imaging sensor that acquires a fluorescence image by capturing fluorescence generated at the imaging subject due to the irradiation with the excitation light emitted from the excitation light source; and a processor comprising hardware, the processor being configured to implement:
adjusting a number of pixels for binning summing and/or an exposure time for the imaging sensor on the basis of luminance information of the fluorescence image acquired by the imaging sensor so that an SN ratio of the fluorescence image becomes equal to or higher than a predetermined threshold;
calculating an incident light level on the imaging sensor based on the luminance information; and
storing a correspondence relationship between the incident light level on the imaging sensor and the number of pixels for binning summing,
wherein the number of pixels for binning summing is determined based on the stored correspondence relationship by using the calculated incident light level.

2. A fluorescence observation apparatus according to claim 1, wherein the processor is further configured to implement:
setting of the predetermined threshold, and
storing a correspondence relationship between the incident light level on the imaging sensor and the SN ratio for each number of pixels for binning summing.

3. A fluorescence observation apparatus comprising:
an excitation light source that emits excitation light to be radiated onto an imaging subject;
a fluorescence-image acquisition portion that is provided with an imaging sensor that acquires a fluorescence image by capturing fluorescence generated at the imaging subject due to the irradiation with the excitation light emitted from the excitation light source; and
a processor comprising hardware, the processor being configured to implement:
adjusting a number of pixels for binning summing and/or an exposure time for the imaging sensor on the basis of luminance information of the fluorescence image acquired by the imaging sensor so that an SN ratio of the fluorescence image becomes equal to or higher than a predetermined threshold,
calculating an incident light level on the imaging sensor based on the luminance information; and
storing a correspondence relationship between the incident light level on the imaging sensor and the exposure time, and
wherein the exposure time is determined based on the stored correspondence relationship by using the calculated incident light level.

4. A fluorescence observation apparatus according to claim 3, wherein the processor is further configured to implement:
setting the predetermined threshold, and
storing a correspondence relationship between the incident light level on the imaging sensor and the SN ratio, for each exposure time.

5. A fluorescence observation apparatus comprising:
an excitation light source that emits excitation light to be radiated onto an imaging subject;
a fluorescence-image acquisition portion that is provided with an imaging sensor that acquires a fluorescence image by capturing fluorescence generated at the imaging subject due to the irradiation with the excitation light emitted from the excitation light source; and
a processor comprising hardware, the processor being configured to implement:
adjusting a number of pixels for binning summing and/or an exposure time for the imaging sensor on the basis of luminance information of the fluorescence image acquired by the imaging sensor so that an SN ratio of the fluorescence image becomes equal to or higher than a predetermined threshhold,
calculating, based on the luminance information, an imaging-surface illuminance which is an incident light level on the imaging sensor per unit time; and
storing correspondence relationships between the imaging-surface illuminance of the imaging sensor and the number of pixels for binning summing, as well as the exposure time, and
wherein the number of pixels for binning summing and the exposure time are determined from the stored correspondence relationship by using the calculated imaging-surface illuminance.

6. A fluorescence observation apparatus according to claim 5, further comprising:
an illumination light source that emits illumination light to be radiated onto the imaging subject; and
the processor is further configured to implement:
acquiring a reference image by capturing reflected light coming from the imaging subject due to the illumination light from the illumination light source,
storing correspondence relationships between the imaging-surface illuminance at the imaging sensor and the number of pixels for binning summing, as well as the exposure time for each blurring level of the reference image; and
determining the number of pixels for binning summing and the exposure time by using the correspondence relationship selected in accordance with the blurring level calculated based on the acquired luminance information of the reference image.

7. A fluorescence observation apparatus according to claim 5, further comprising:
an illumination light source that emits illumination light to be radiated onto the imaging subject; and
the processor is further configured to implement:
acquiring a reference image by capturing reflected light coming from the imaging subject due to the illumination light from the illumination light source,
storing correspondence relationships between the imaging-surface illuminance at the imaging sensor and the number of pixels for binning summing, as well as the exposure time for each luminance of the reference image; and
determining the number of pixels for binning summing and the exposure time by using the correspondence relationship selected in accordance with the acquired luminance information of the reference image.

8. A fluorescence observation apparatus according to claim 2, wherein the processor is further configured to implement:
calculating a contrast of the fluorescence image based on the luminance information of the fluorescence image acquired by the fluorescence-image acquisition portion, and
setting the threshold on the basis of the calculated contrast.

9. A fluorescence observation apparatus according to claim 4, wherein the processor is further configured to implement:
calculating a contrast of the fluorescence image based on the luminance information of the fluorescence image acquired by the fluorescence-image acquisition portion, and
setting the threshold on the basis of the calculated contrast.

10. A fluorescence observation apparatus according to claim 2, further comprising:
an illumination light source that emits illumination light to be radiated onto the imaging subject; and
the processor is further configured to implement
acquiring a reference image by capturing reflected light coming from the imaging subject due to the illumination light from the illumination light source, and
setting the threshold on the basis of the acquired luminance information of the reference image.

11. A fluorescence observation apparatus according to claim 4, further comprising:
an illumination light source that emits illumination light to be radiated onto the imaging subject; and
the processor is further configured to implement:
acquiring a reference image by capturing reflected light coming from the imaging subject due to the illumination light from the illumination light source, and
setting the threshold on the basis of the acquired luminance information of the reference image.

12. A fluorescence observation apparatus according to claim 1, further comprising:
a display that displays the fluorescence image; and
the processor is further configured to implement:
correcting the brightness of the acquired fluorescence image on the basis of the calculated incident light level and
outputting the image to the display.

13. A fluorescence observation apparatus according to claim 1, further comprising:
an attached/detached part that stores identification information and that is attached/detached to change observation conditions; and
an identification-information reader that reads the identification information stored in the attached/detached part,
wherein the the processor is further configured to implement:
storing a correspondence relationship between the incident light level on the imaging sensor and the number of pixels for binning summing for each piece of identification information; and
selecting the correspondence relationship on the basis of the identification information read by the identification-information reader.

* * * * *